United States Patent
Yan et al.

(10) Patent No.: US 10,240,988 B2
(45) Date of Patent: Mar. 26, 2019

(54) FULLY AUTOMATED CALIBRATION FOR ACOUSTIC PYROMETRY

(71) Applicant: Siemens Energy, Inc., Orlando, FL (US)

(72) Inventors: Michelle xiaohong Yan, Princeton, NJ (US); Heiko Claussen, North Brunswick, NJ (US); Upul P. DeSilva, Oviedo, FL (US); Justinian Rosca, West Windsor, NJ (US); Tong Fang, Morganville, NJ (US); Nancy H. Ulerich, Longwood, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 536 days.

(21) Appl. No.: 14/894,010

(22) PCT Filed: May 29, 2014

(86) PCT No.: PCT/US2014/039971
§ 371 (c)(1),
(2) Date: Nov. 25, 2015

(87) PCT Pub. No.: WO2014/194056
PCT Pub. Date: Dec. 4, 2014

(65) Prior Publication Data
US 2016/0109304 A1    Apr. 21, 2016

Related U.S. Application Data (60) Provisional application No. 61/828,936, filed on May 30, 2013.

(51) Int. Cl.
*G01N 29/024*   (2006.01)
*G01K 11/24*    (2006.01)
(Continued)

(52) U.S. Cl.
CPC ............ *G01K 15/005* (2013.01); *G01K 11/24* (2013.01); *G01K 13/02* (2013.01);
(Continued)

(58) Field of Classification Search
CPC .. G10K 11/178; G10K 11/008; G01N 29/024; G01N 2291/02881; G01K 11/24
(Continued)

(56) References Cited

U.S. PATENT DOCUMENTS 6,834,992 B2 * 12/2004 Draxton ................. G01K 11/24
                                                              181/142
8,256,953 B2 *  9/2012 Yuhas ..................... G01K 17/00
                                                               374/29
(Continued)

FOREIGN PATENT DOCUMENTS

EP      1785701  A1   5/2007

OTHER PUBLICATIONS

PCT International Search Report dated Nov. 6, 2014 corresponding to PCT International Application No. PCT/US2014/039971 filed May 29, 2014 (13 pages).

*Primary Examiner* — Gail Kaplan Verbitsky (57) ABSTRACT

A method of calibrating transceiver positions inside an acoustic pyrometry measuring vessel that contains a plurality of transceivers, includes determining (40) a speed of sound in the acoustic pyrometry measuring vessel from a temperature and gas composition of a gas inside the acoustic pyrometry measuring vessel, acquiring (41) time-of-flight (TOFs) $\Delta t_{i,j}$ measurements from a plurality of pairs i,j of transceivers inside the acoustic pyrometry measuring vessel, estimating (42) a radius of the acoustic pyrometry measuring vessel from an average of the acquired TOF measurements, (Continued)

and using (43) an estimated radius of the acoustic pyrometry measuring vessel to estimate errors $\Delta\theta j$ of displacement angles of the transceivers.

13 Claims, 5 Drawing Sheets

(51) Int. Cl.
*G01K 15/00* (2006.01)
*G01K 13/02* (2006.01)

(52) U.S. Cl.
CPC ... *G01K 2013/024* (2013.01); *G01K 2205/04* (2013.01); *G01N 2291/02881* (2013.01)

(58) Field of Classification Search
USPC .... 374/117–119, 6, 141, 120, 1, 45; 356/43, 356/44
See application file for complete search history.

(56) References Cited

U.S. PATENT DOCUMENTS

| | | | |
|---|---|---|---|
| 8,565,999 B2* | 10/2013 | Bunce | F02C 9/28 701/1 |
| 9,453,784 B2* | 9/2016 | DeSilva | G01K 11/24 |
| 9,702,768 B2* | 7/2017 | Claussen | G01K 11/24 |
| 9,945,737 B2* | 4/2018 | DeSilva | G01K 1/20 |
| 2012/0150413 A1* | 6/2012 | Bunce | F02C 9/28 701/100 |
| 2013/0306375 A1* | 11/2013 | Rasheed | E21B 10/32 175/45 |

* cited by examiner

FULLY AUTOMATED CALIBRATION FOR ACOUSTIC PYROMETRY

CROSS REFERENCE TO RELATED UNITED STATES APPLICATIONS

This application claims priority from "FULLY AUTOMATED CALIBRATION SYSTEM FOR ACOUSTIC PYROMETRY", U.S. Provisional Application No. 61/828,936 of Yan, et al., filed May 30, 2013, the contents of which are herein incorporated by reference in their entirety.

This patent application is based upon work supported by the Department of Energy under Award Number DE-FC26-05NT42644.

TECHNICAL FIELD

This disclosure is directed to methods and systems for acoustic pyrometry.

DISCUSSION OF THE RELATED ART

Acoustic pyrometry is the process of using sound waves to measure temperature inside an object. The principles involved in acoustic pyrometry are straightforward. A pyrometer measures the time-of-flight (TOF) of acoustic waves traveling between a fixed sound source (transmitter) and microphone (receiver) pair. When the distance between the two fixed points is known, the speed of sound C traveling in the medium can be computed, and the average temperature T in Kelvin of the path traversed by the sound wave can be computed using $$C = \sqrt{\frac{\gamma RT}{m}}, \quad (1)$$

where $\gamma$ is the ratio between the specific heats of the gas at constant pressure and constant volume, R is the gas constant and m is the molecular weight of the gas. In principle, if a sufficient number of TOF measurements are available in conjunction with knowledge of the paths traversed by sound waves, tomographic reconstruction can be used to generate a temperature distribution map of the acoustic traveling plane.

However, this method is challenging in practice. There are various sources of errors and uncertainties that complicate acoustic tomographic reconstruction and make temperature measurement less accurate. For example, it is well understood that uncertainties in TOF measurements are the main factor that affects the accuracy of temperature measurements. In addition, the paths traversed by sound waves from transmitter to receiver are not known exactly due to the bending of sound propagation in flowing air or fluid. However, straight lines are used in most cases where the error introduced is insignificant. In addition, measurements of the locations or coordinates of end points of each sound path are not truly accurate due to error margins allowed during the mounting of transmitters and receivers, and due to minor discrepancies in the geometric descriptions of a furnace or exhaust vent. Thus, these measurements may differ from what are actually in use. These discrepancies do not change over time or due to different operational conditions, however, they do introduce an offset or bias to the actual temperature measurement.

SUMMARY

Exemplary embodiments of the invention as described herein are directed to a fully automatic calibration system that can accurately measure the locations or coordinates of end points of each sound path. Furthermore, a calibration algorithm and system according to an embodiment of the invention can be directly applied to other pyrometry applications when system calibration is necessary.

According to an embodiment of the invention, there is provided a method of calibrating transceiver positions inside an acoustic pyrometry measuring vessel that contains a plurality of transceivers, including acquiring time-of-flight (TOFs) $\Delta t_{i,j}$ measurements from a plurality of pairs i,j of transceivers inside the acoustic pyrometry measuring vessel, and using an estimated radius of the acoustic pyrometry measuring vessel to estimate errors $\Delta \theta_j$ of displacement angles of the transceivers.

According to a further embodiment of the invention, the method includes estimating a radius of the acoustic pyrometry measuring vessel from an average of the acquired TOF measurements.

According to a further embodiment of the invention, the method includes repeating the steps of estimating a radius of the acoustic pyrometry measuring vessel and using the estimated radius to estimate errors $\Delta \theta_j$ of displacement angles until convergence.

According to a further embodiment of the invention, the radius $r_i$ of each transceiver the acoustic pyrometry measuring vessel is estimated from $$\frac{C_0}{(N-1)} \sum_{i=1,i\neq j}^{N} \frac{\Delta t_{i,j}}{2\sin\left(\frac{|\theta_i - \theta_j|}{2}\right) + (\Delta\theta_i - \Delta\theta_j)\cos\left(\frac{|\theta_i - \theta_j|}{2}\right)},$$

where $C_0$ is a speed of sound, N is a number of transceivers, and $\theta_i$ is a displacement angle of transceiver i.

According to a further embodiment of the invention, the method includes determining a speed of sound in the acoustic pyrometry measuring vessel from a temperature and gas composition of a gas inside the acoustic pyrometry measuring vessel.

According to a further embodiment of the invention, the speed of sound C in the acoustic pyrometry measuring vessel is determined from $$C = \sqrt{\frac{\gamma RT}{m}},$$

where T is the temperature T in degrees Kelvin, $\gamma$ is a ratio between specific heats of the gas at constant pressure and constant volume, R is the gas constant, and m is a molecular weight of the gas.

According to a further embodiment of the invention, errors $\Delta \theta_j$ of displacement angles of the transceivers are estimated from $$(\Delta\theta_i - \Delta\theta_j)\cos\left(\frac{|\theta_i - \theta_j|}{2}\right) = \frac{\Delta t_{i,j} C_0}{r} - 2\sin\left(\frac{\theta_i - \theta_j}{2}\right),$$

where $C_0$ is a speed of sound, r is the estimated radius, and $\hat{\theta}_i$ is an intended angle of transceiver i.

According to a further embodiment of the invention, the errors $\Delta\theta j$ of displacement angles of the transceivers are estimated using a least squares fit.

According to another embodiment of the invention, there is provided a system for calibrating transceiver positions for acoustic, including an acoustic pyrometry measuring vessel, a plurality of transceivers disposed about a perimeter of the measuring vessel, the transceivers configured to transmit an acoustic wave signal upon receipt of an electric signal and to receive acoustic wave signals and convert a received acoustic wave signal into an electric signal, and a computer processor configured to transmit and receive the electric signals sent to and received from the transceivers, to determine time-of-flight (TOFs) $\Delta t i_{,j}$ measurements from each pair i,j of transceivers inside the acoustic pyrometry measuring vessel, to estimate a radius of the acoustic pyrometry measuring vessel from an average of the acquired TOF measurements, and to use the estimated radius of the acoustic pyrometry measuring vessel to estimate errors $\Delta\theta j$ of displacement angles of the transceivers.

According to a further embodiment of the invention, the computer processor is configured to determine a speed of sound in the acoustic pyrometry measuring vessel from a temperature and gas composition of a gas inside the acoustic pyrometry measuring vessel.

According to another embodiment of the invention, there is provided a non-transitory program storage device readable by a computer, tangibly embodying a program of instructions executed by the computer to perform the method steps for calibrating transceiver positions inside an acoustic pyrometry measuring vessel that contains a plurality of transceivers.

DETAILED DESCRIPTION OF EXEMPLARY EMBODIMENTS

Exemplary embodiments of the invention as described herein generally include systems and methods for measuring the locations or coordinates of end points of each sound path in an acoustic pyrometry system. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

Figure 1:
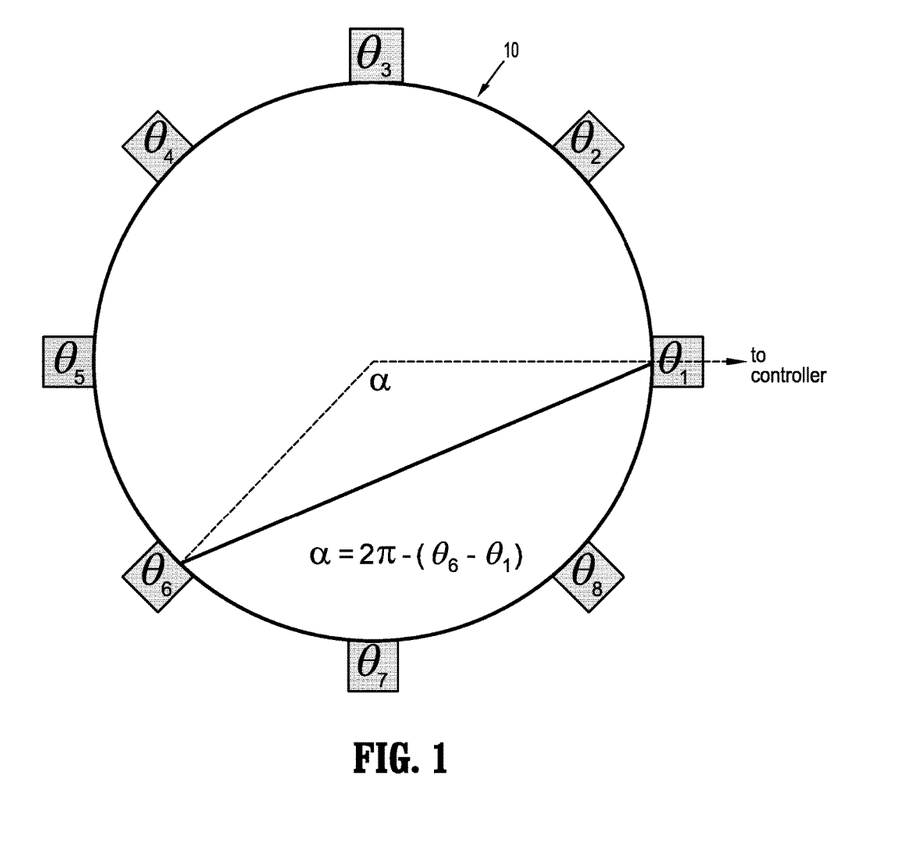
FIG. 1 illustrates the distribution of eight transceivers inside a vessel of radius R, where $\theta_i$ depicts the location of transceiver i, according to an embodiment of the invention.
Figure 5:
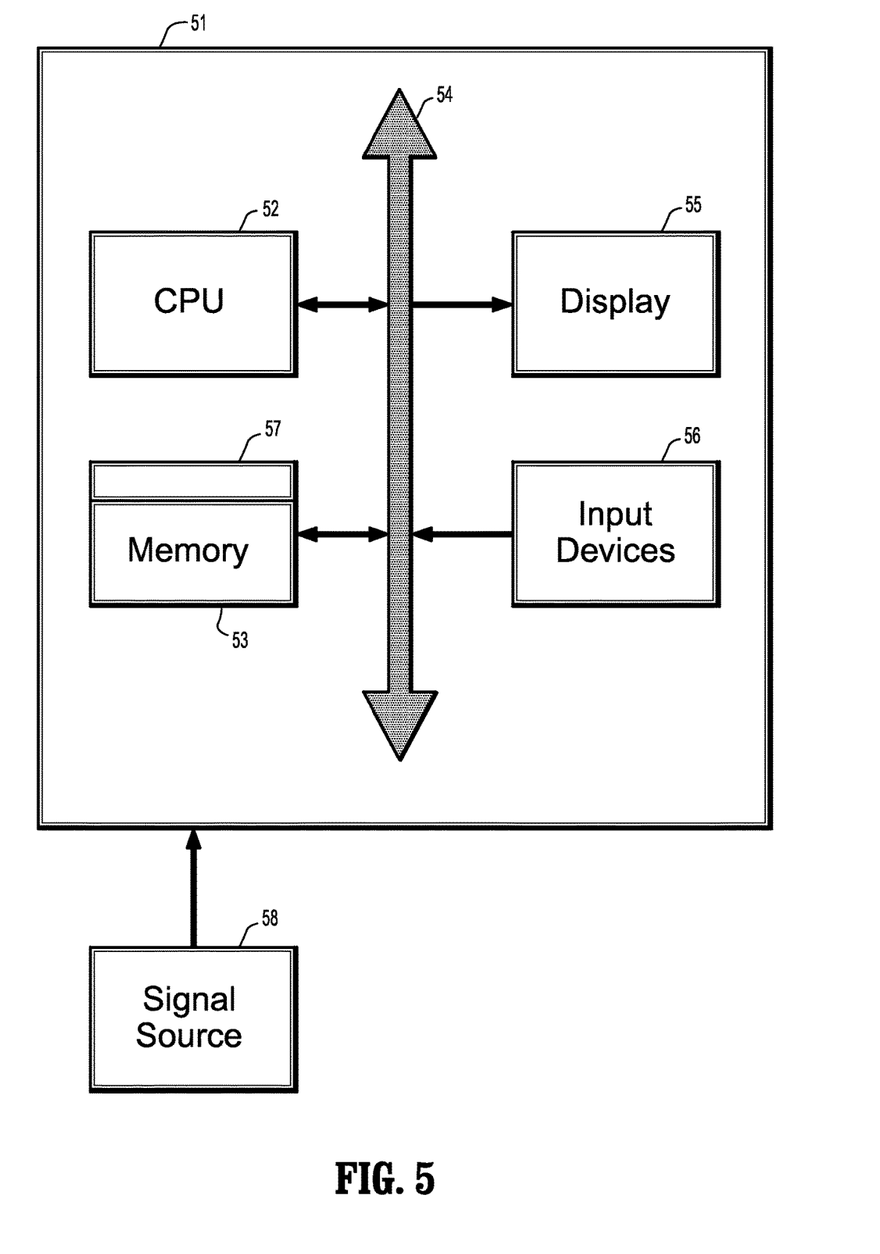
FIG. 5 is a block diagram of an exemplary computer system for implementing a method for auto-calibration of the locations or coordinates of end points of each sound path, according to an embodiment of the invention.

When an off-line gas turbine is placed in a room at a constant temperature $T_0$ for a time, as a result, the inside of the furnace or exhaust will equilibrate to have the same temperature $T_0$. Using EQ. (1), one can compute the sound speed $C_0$ in the medium with temperature $T_0$. FIG. 1 is a schematic illustration of a plurality of transceivers that are distributed along the inside of an outer wall of a vessel 10 according to an embodiment of the invention. The transceivers are in signal communication with an external controller, such as a computer. An exemplary computer system for controlling the transceivers is depicted in FIG. 5, described below. According to an embodiment of the invention, the vessel can modeled as a cylinder with a radius r, as illustrated in FIG. 1, which for demonstration purposes depicts eight transceivers $\theta_i$, where each transceiver location is denoted by central angle $\theta_i$, i=1, . . . , 8. The distance between any pair of transceivers can be calculated from the law of cosines from the angle $\alpha$ formed between the radii extending from the center to the respective transceivers, where $\alpha=2\pi-(\theta_j-\theta_i)$. Let $\Delta t_{i,j}$ denote the TOF measurement from transmitter i to receiver j. Thus, the TOF measurement and constant temperature information can be used to automatically calibrate the transceiver coordinates and exhaust geometry to improve the accuracy of the temperature estimation. To simplify the demonstration, all transceivers may be assumed to be the same distance r from the center of the exhaust, i.e., there is no displacement distance for the transceivers.

As seen in FIG. 1, the use of trigonometry yields the following equality:

$$\sin\left(\frac{\theta_i - \theta_j}{2}\right) = \frac{\Delta t_{i,j} C_0}{2r}, \ i, j = 1, \ldots, 8, \tag{2}$$

where i must be greater than j for $\theta_i > \theta_j$ and value on the left side of EQ. (2) to be non-negative, thus EQ. (2) is valid for all i and j. To take into account the uncertainty or allowed error margin during installation, each transceiver location can be modeled as $$\theta_i = \hat{\theta}_i + \Delta\theta_i, i=1, \ldots, 8,$$

where $\hat{\theta}_i$ denotes an expected or intended location for $\theta_i$, for example, $\hat{\theta}_i = (i-1) \times 45°$, i=1, . . . 8, i.e., all transceivers are uniformly distributed along a circle. After keeping linear terms of a Taylor expansion of EQ. (2) at $(\hat{\theta}_i - \hat{\theta}_j)/2$ and re-arranging the terms, the first order approximation becomes:

$$(\Delta\theta_i - \Delta\theta_j)\cos\left(\frac{\hat{\theta}_i - \hat{\theta}_j}{2}\right) = \frac{\Delta t_{i,j} C_0}{r} - 2\sin\left(\frac{\hat{\theta}_i - \hat{\theta}_j}{2}\right), \tag{3}$$

$$i, j = 1, \ldots, 8,$$

which is a linear function of $\Delta\theta_i$ for i=1, . . . , 8. Hence with EQ. (3), one can easily estimate $\Delta\theta_i$ using least squares to fit, therefore $\theta_i$, i=1, . . . , 8, for a given radius r.

In addition, distance displacements of transceivers can be estimated as well. Instead of having the same R for all transceivers, each transceiver would be described by two parameters $\{r_i, \theta_i\}$, i=1, . . . , 8, and both sets of parameters $\{r_i, i=1, \ldots, 8\}$ and $\{\theta_i, i=1, \ldots, 8\}$ would be estimated iteratively using a least squares method, given the corresponding TOF measurements. For example, starting with an initial guess as $\theta_i=(i-1)\times45°$, $i=1, \ldots, 8$, and setting $\Delta\theta_i=0$, the radius $r_i$ can then be estimated by averaging results from each sound traversed path passing through $\theta_i$. Then, with the estimated radius $r_i$, $\Delta\theta_i$, $i=1, \ldots, 8$ can be found using least squares. This procedure converges quickly and may be repeated for 2 or 3 times. According to an embodiment of the invention, another approximation is introduced; assume that all $r_i$, $i=1, \ldots, 8$, are approximately equal, such that the linear approximation of EQ. (3) still holds.

An experiment to test and validate an automated calibration system according to an embodiment of the invention can be designed as follows. A gas turbine is placed in a room with a temperature of 8.76° C., equivalent to 281.76° K. Using EQ. (1) with a gas constant R=287 and the ratio $\gamma/m=1.4$, the sound travels at a speed of 336.47 m/s in the exhaust. The TOF measurements among all different sound traversed paths are estimated using an approach disclosed in U.S. patent application Ser. No. 13/961,292, "Noise Robust Time of Flight Estimation for Acoustic Pyrometry", filed on Aug. 7, 2013, assigned to the assignee of the present application, the contents of which are herein incorporated by reference in their entirety.

Figure 4:
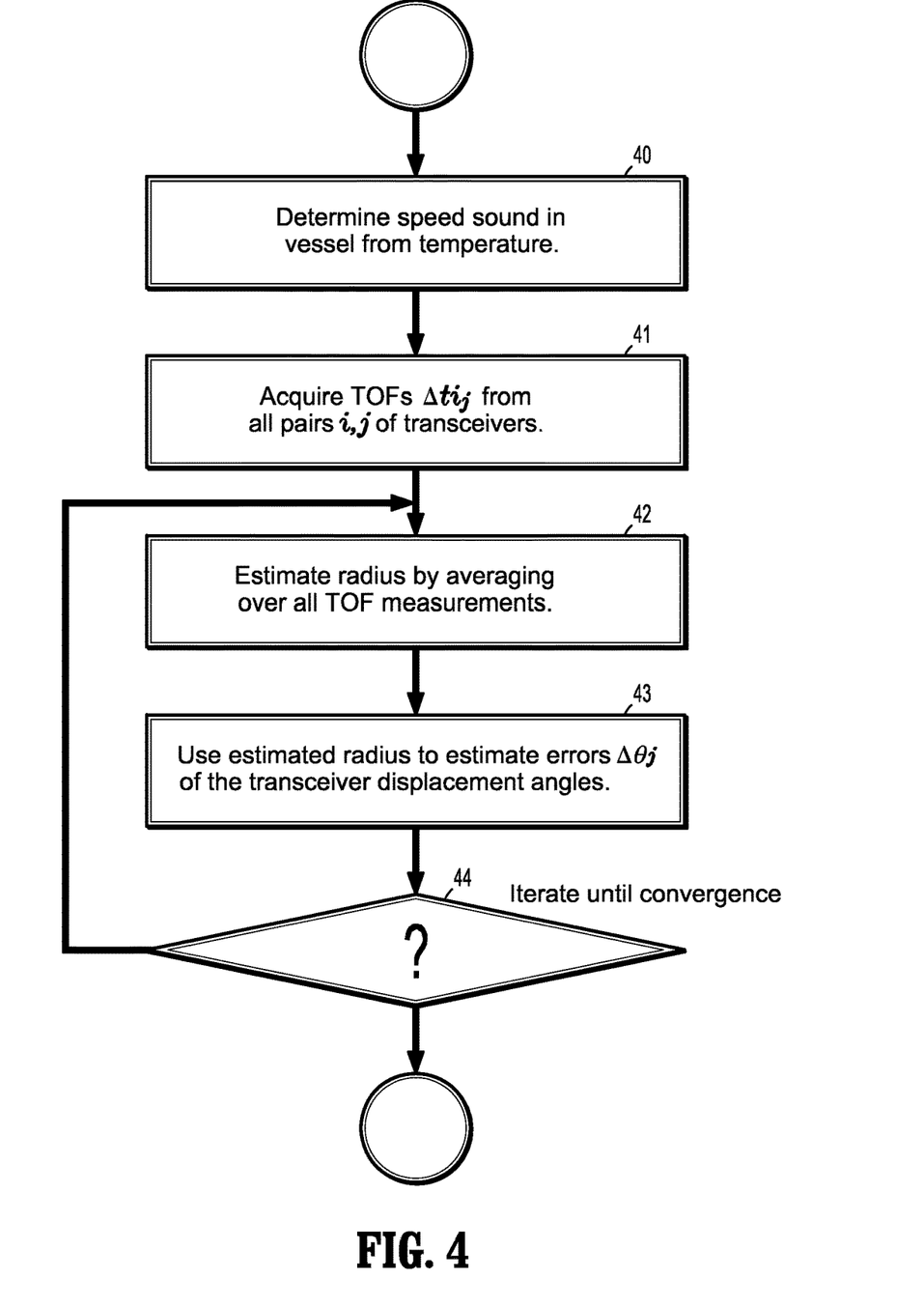
FIG. 4 is a flow chart of a method for auto-calibration of the locations or coordinates of end points of each sound path, according to an embodiment of the invention.

FIG. 4 is a flow chart of a method for auto-calibration of the locations or coordinates of end points of each sound path, according to an embodiment of the invention. As disclosed above, a container or vessel containing a gas of known composition is placed inside a room of known temperature and allowed to equilibrate. Referring now to the figure, a method begins at step 40 by determining the speed of sound $C_0$ in the vessel from the temperature. The container includes a plurality of transceivers on the perimeter in positions that are approximately known. A electronic controller sends electronic signals to the transceivers to initiate transmission of acoustic signals, and receives an electronic signal from each transceiver when the transceiver receives an acoustic signal. An exemplary, non-limiting electronic controller is a digital computer, and the electronic signals may be digital electronic signals. The digital computer may be configured to perform the following computations. Then, at step 41 TOFs $\Delta t_{i,j}$ are acquired from all pairs i,j of transceivers. In the example of FIG. 1, in which there are N=8 transceivers, there are $N(N-1)/2=28$ such pairs. According to an embodiment of the invention, an acoustic wave is sent from one transceiver at a time, and signals are recorded from each of the remaining transceivers upon receipt of the acoustic wave, before sending an acoustic wave from another transceiver. The TOFs $\Delta t_{i,j}$ can be determined from the time a transmit signal was sent to the transmitting transceiver, and the time a signal was received from each receiving transceiver indicating receipt of an acoustic signal. At step 42, the radius $r_i$ of each transceiver can be estimated by an average over all TOF measurements:

$$r_i = C_0 \left\langle \frac{\Delta t_{i,j}}{2\sin\left(\frac{|\theta_i - \theta_j|}{2}\right) + (\Delta\theta_i - \Delta\theta_j)\cos\left(\frac{\theta_i - \theta_j}{2}\right)} \right\rangle \quad (4)$$

$$= \frac{C_0}{(N-1)} \sum_{i=1, i\neq j}^{N} \frac{\Delta t_{i,j}}{2\sin\left(\frac{|\theta_i - \theta_j|}{2}\right) + (\Delta\theta_i - \Delta\theta_j)\cos\left(\frac{\theta_i - \theta_j}{2}\right)},$$

where the brackets < > indicate an arithmetic mean over transceiver i. The estimated values of all $r_i$ can be used at step 43 to estimate errors $\Delta\theta j$ of the displacement angles of the transceivers from EQ. (3), above. An exemplary, non-limiting method of estimating the errors $\Delta\theta j$ from EQ. (3) is a linear least squares. Step 42 can then be repeated, adjusting the displacement angles $\theta_j$ with the corrections calculated in step 43, and step 43 can be repeated with the new radius value $r_i$ of transceiver i These steps can be repeated from step 44 until convergence.

To demonstrate a need for auto-calibration, about a 2% error was added to the exhaust diameter 5.93 m, which becomes about 6.03 m. Thus, instead of 5.93 m, 6.03 m was used as the input diameter to an auto-calibration system according to an embodiment of the invention to determine the effect on estimated temperatures with and without calibration. In this experiment, all transceivers are evenly mounted along the wall of a circular exhaust outlet. Therefore, a fixed reference point was chosen in the implementation, as otherwise, estimated angle locations would become unstable—the transceivers could move around along the circle by keeping the same angle difference with respect to its neighboring point. Here $\theta_1$ was chosen as the reference point, and as a result $\Delta\theta_1$ will always equal zero. The initial guess for $\Delta\theta_i=0$, $i=1, \ldots, 8$ was used as an input to the system, and an initial temperature of 300° K was used in this experiment.

Figure 2:
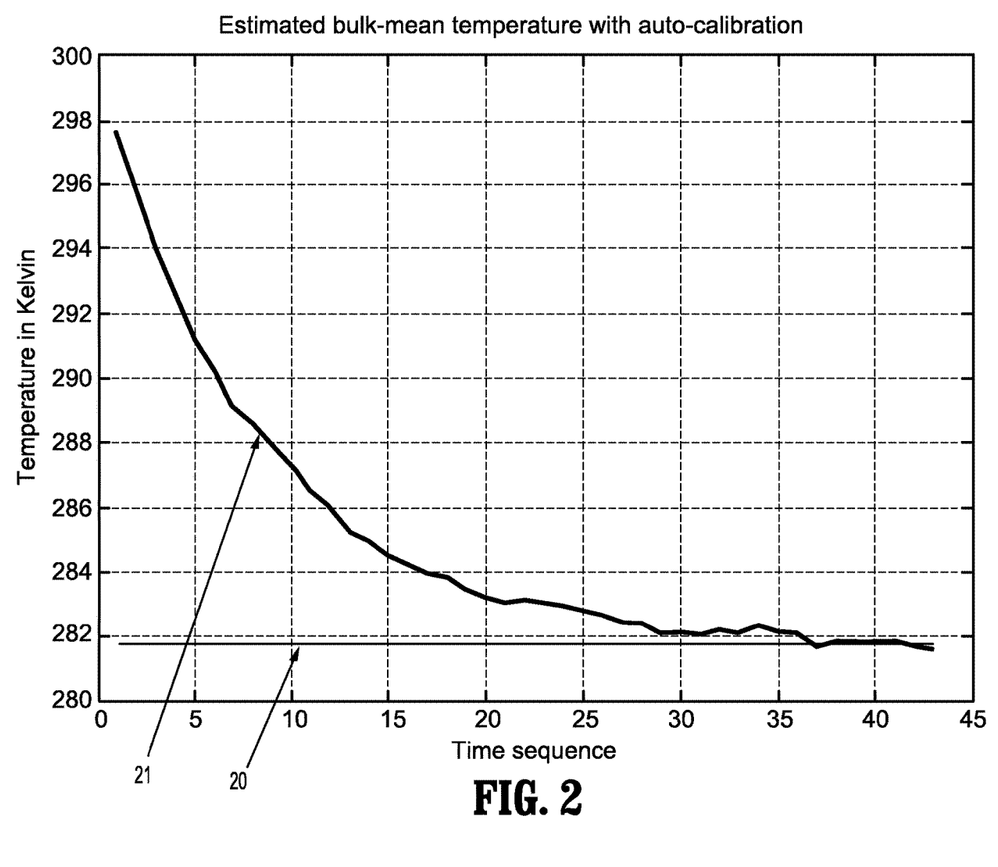
FIG. 2 illustrates the temperature estimation convergence without autocalibration, according to an embodiment of the invention.
Figure 3:
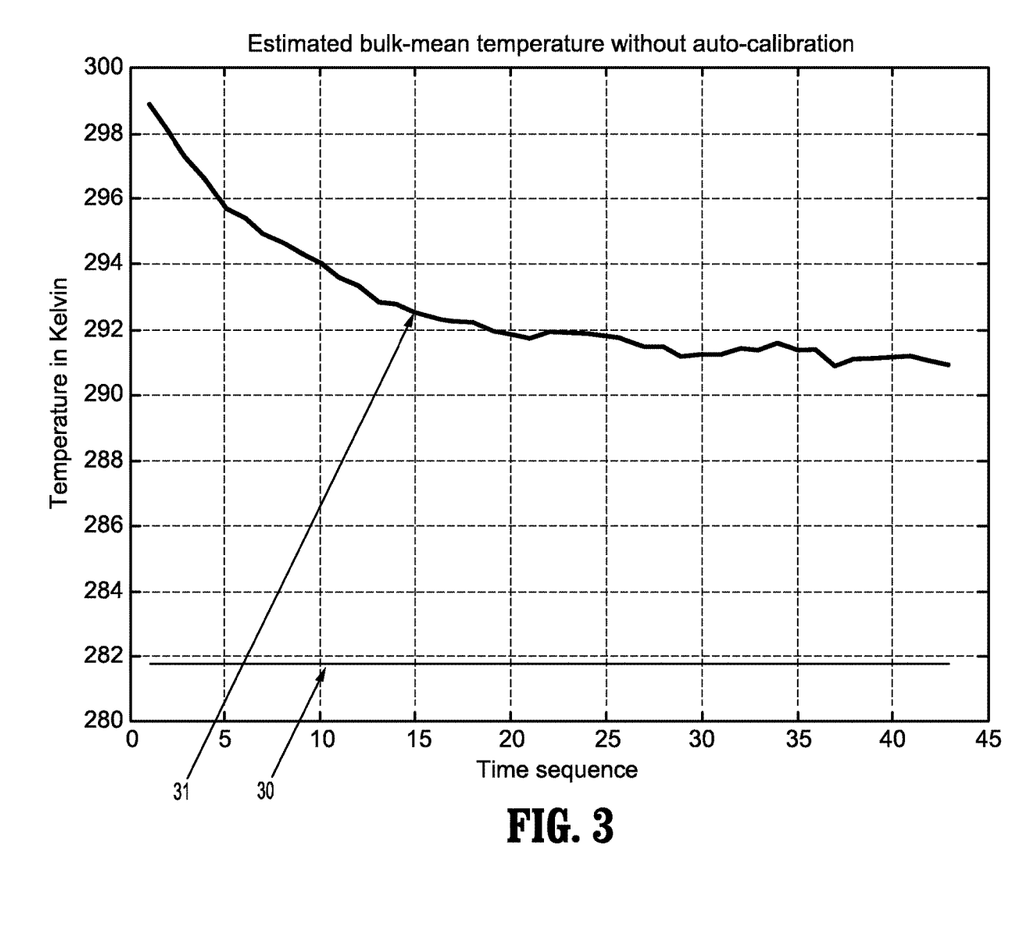
FIG. 3 illustrates temperature estimation convergence with auto-calibration, according to an embodiment of the invention.

FIG. 2 shows estimated temperatures 21 over time without auto-calibration, i.e. using the 9 input parameters describing location and geometry, without further verifying with the TOF measurements. The true temperature is indicted by line 20. It clearly shows that as the estimated temperature converges, it is about 10° K higher the true temperature T=281.76° K. On the other hand, FIG. 3 depicts estimated temperatures 31 over time with an auto-calibration according to an embodiment of the invention, where the system takes the 9 input parameters as an initial guess, and validates with the TOF measurements by using those TOF measurements to refine the nine parameters: the diameter of exhaust outlet r and the transceiver locations $\theta_i$, $i=1, \ldots, 8$. Furthermore, FIG. 3 shows how the estimated temperature converges to the true temperature T=281.76° K. The true temperature is indicted by line 30. The refined diameter after auto-calibration is 5.93 m, which is the same as that originally provided. The maximum deviation from the expected central angles after auto-calibration is about 0.5°, which indicates the transceivers are mounted accurately.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

FIG. 5 is a block diagram of an exemplary computer system for controlling the transceivers depicted in FIG. 1 and implementing a method for auto-calibration of the locations or coordinates of end points of each sound path, according to an embodiment of the invention. Referring now to FIG. 5, a computer system 51 for implementing the present invention can comprise, inter alia, a central processing unit (CPU) 52, a memory 53 and an input/output (I/O) interface 54. The computer system 51 is generally coupled through the I/O interface 54 to a display 55 and various input devices 56 such as a mouse and a keyboard. The support circuits can include circuits such as cache, power supplies, clock circuits, and a communication bus. The memory 53 can include random access memory (RAM), read only memory (ROM), disk drive, tape drive, etc., or a combinations thereof. The present invention can be implemented as a routine 57 that is stored in memory 53 and executed by the CPU 52 to process the signal from the signal source 58. As such, the computer system 51 is a general purpose computer system that becomes a specific purpose computer system when executing the routine 57 of the present invention.

The computer system 51 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A computer implemented method of calibrating transceiver positions inside an acoustic pyrometry measuring vessel that contains a plurality of transceivers, the method executed by the computer comprising the steps of:
   placing the acoustic pyrometry measuring vessel in a space of a known constant temperature containing a gas of known composition and allowing the acoustic pyrometry measuring vessel to equilibrate;
   determining a speed of sound in said acoustic pyrometry measuring vessel from the known constant temperature and the known gas composition of the gas inside said acoustic pyrometry measuring vessel;
   acquiring time-of-flight (TOFs) $\Delta t_{i,j}$ measurements from a plurality of pairs i,j of transceivers inside said acoustic pyrometry measuring vessel;
   estimating a radius of said acoustic pyrometry measuring vessel from an average of the acquired TOF measurements; and
   using the estimated radius of said acoustic pyrometry measuring vessel to estimate errors $\Delta\theta j$ of displacement angles of the transceivers,
   wherein the errors $\Delta\theta j$ of displacement angles of the transceivers from the calibration are utilized to accurately determine a temperature within the acoustic pyrometry measuring vessel when the temperature inside the acoustic pyrometry measuring vessel is not known, and
   wherein the determined temperature within the acoustic pyrometry measuring vessel is displayed on a display.

2. The method of claim 1, further comprising repeating said steps of estimating a radius of said acoustic pyrometry measuring vessel and using said estimated radius to estimate errors $\Delta\theta j$ of displacement angles until convergence.

3. The method of claim 1, wherein the radius $r_i$ of each transceiver of said acoustic pyrometry measuring vessel is estimated from the average over all TOF measurements:

$$\frac{C_0}{(N-1)} \sum_{i=1, i \neq j}^{N} \frac{\Delta t_{i,j}}{2\sin\left(\frac{|\hat{\theta}_i - \hat{\theta}_j|}{2}\right) + (\Delta\theta_i - \Delta\theta_j)\cos\left(\frac{\hat{\theta}_i - \hat{\theta}_j}{2}\right)},$$

wherein $C_0$ is a speed of sound, N is a number of transceivers, and $\theta_i$ is a displacement angle of transceiver i.

4. The method of claim 1, wherein the speed of sound C in said acoustic pyrometry measuring vessel is determined from $$C = \sqrt{\frac{\gamma RT}{m}},$$

where T is the temperature T in degrees Kelvin, $\gamma$ is a ratio between specific heats of the gas at constant pressure and constant volume, R is the gas constant, and m is a molecular weight of the gas.

5. The method of claim 1, wherein errors $\Delta\theta j$ of displacement angles of the transceivers are estimated from $$(\Delta\theta_i - \Delta\theta_j)\cos\left(\frac{\hat{\theta}_i - \hat{\theta}_j}{2}\right) = \frac{\Delta t_{i,j} C_0}{r} - 2\sin\left(\frac{\hat{\theta}_i - \hat{\theta}_j}{2}\right),$$

wherein $C_0$ is a speed of sound, r is the estimated radius, and $\hat{\theta}_i$ is an intended angle of transceiver i.

6. The method of claim 5, wherein the errors $\Delta\theta j$ of displacement angles of the transceivers are estimated using a least squares fit.

7. A system for calibrating transceiver positions for acoustic pyrometry, comprising:
   an acoustic pyrometry measuring vessel;
   a plurality of transceivers disposed about a perimeter of said measuring vessel, said transceivers configured to transmit an acoustic wave signal upon receipt of an electric signal and to receive acoustic wave signals and convert a received acoustic wave signal into an electric signal; and
   a computer processor configured to automatically perform the calibration by transmitting and receiving the electric signals sent to and received from the transceivers, determining time-of-flight (TOFs) $\Delta t_{i,j}$ measurements from each pair i,j of transceivers inside said acoustic pyrometry measuring vessel, to estimate a radius of said acoustic pyrometry measuring vessel from an average of the acquired TOF measurements, and to using the estimated radius of said acoustic pyrometry measuring vessel to estimate errors $\Delta\theta j$ of displacement angles of the transceivers,
   wherein said computer processor is configured to determine a speed of sound in said acoustic pyrometry measuring vessel from placement of the acoustic pyrometry measuring vessel in a known constant temperature and a known gas composition of a gas inside said acoustic pyrometry measuring vessel,
   wherein the errors $\Delta\theta j$ of displacement angles of the transceivers from the calibration are utilized to accurately determine a temperature within the acoustic pyrometry measuring vessel when the temperature inside the acoustic pyrometry measuring vessel is not known, and wherein the determined temperature within the acoustic pyrometry measuring vessel is displayed on a display.

8. A non-transitory program storage device readable by a computer, tangibly embodying a program of instructions executed by the computer to perform the method steps for calibrating transceiver positions inside an acoustic pyrometry measuring vessel that contains a plurality of transceivers, the method comprising the steps of:
placing the acoustic pyrometry measuring vessel in a space of a known constant temperature containing a gas of known composition and allowing the acoustic pyrometry measuring vessel to equilibrate
determining a speed of sound in said acoustic pyrometry measuring vessel from the known constant temperature and the constant gas composition of the gas inside said acoustic pyrometry measuring vessel;
acquiring time-of-flight (TOFs) $\Delta t_{i,j}$ measurements from a plurality of pairs i,j of transceivers inside said acoustic pyrometry measuring vessel;
estimating a radius of said acoustic pyrometry measuring vessel from an average of the acquired TOF measurements;
using the estimated radius of said acoustic pyrometry measuring vessel to estimate errors $\Delta\theta j$ of displacement angles of the transceivers; and
utilizing errors $\Delta\theta j$ of displacement angles of the transceivers during the calibration to accurately determine a temperature within the acoustic pyrometry measuring vessel when the temperature inside the acoustic pyrometry measuring vessel is not known,
wherein the determined temperature within the acoustic pyrometry measuring vessel is displayed on a display.

9. The computer readable program storage device of claim 8, the method further comprising repeating said steps of estimating a radius of said acoustic pyrometry measuring vessel and using said estimated radius to estimate errors $\Delta\theta j$ of displacement angles until convergence.

10. The computer readable program storage device of claim 8, wherein the radius $r_i$ of each transceiver said acoustic pyrometry measuring vessel is estimated from the average over all TOF measurements:

$$\frac{C_0}{(N-1)} \sum_{i=1, i \neq j}^{N} \frac{\Delta t_{i,j}}{2\sin\left(\frac{|\hat{\theta}_i - \hat{\theta}_j|}{2}\right) + (\Delta\theta_i - \Delta\theta_j)\cos\left(\frac{\hat{\theta}_i - \hat{\theta}_j}{2}\right)},$$

wherein $C_0$ is a speed of sound, N is a number of transceivers, and $\hat{\theta}_i$ is a displacement angle of transceiver i.

11. The computer readable program storage device of claim 8, wherein the speed of sound C in said acoustic pyrometry measuring vessel is determined from $$C = \sqrt{\frac{\gamma RT}{m}},$$

where T is the temperature T in degrees Kelvin, $\gamma$ is a ratio between specific heats of the gas at constant pressure and constant volume, R is the gas constant, and m is a molecular weight of the gas.

12. The computer readable program storage device of claim 8, wherein errors $\Delta\theta j$ of displacement angles of the transceivers are estimated from $$(\Delta\theta_i - \Delta\theta_j)\cos\left(\frac{\hat{\theta}_i - \hat{\theta}_j}{2}\right) = \frac{\Delta t_{i,j} C_0}{r} - 2\sin\left(\frac{\hat{\theta}_i - \hat{\theta}_j}{2}\right),$$

wherein $C_0$ is a speed of sound, r is the estimated radius, and $\hat{\theta}_i$ is an intended angle of transceiver i.

13. The computer readable program storage device of claim 12, wherein the errors $\Delta\theta j$ of displacement angles of the transceivers are estimated using a least squares fit.

* * * * *